US007157561B2

(12) United States Patent
Hui et al.

(10) Patent No.: US 7,157,561 B2
(45) Date of Patent: Jan. 2, 2007

(54) METHODS OF INHIBITING TRANSMISSION OF A COSTIMULATORY SIGNAL OF LYMPHOCYTES

(75) Inventors: Raymond A. Hui, Indianapolis, IN (US); Richard T. Root, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 57 days.

(21) Appl. No.: 10/982,611

(22) Filed: Nov. 5, 2004

(65) Prior Publication Data

US 2005/0064517 A1    Mar. 24, 2005

Related U.S. Application Data

(63) Continuation-in-part of application No. 10/669,831, filed on Sep. 24, 2003, which is a continuation-in-part of application No. 10/192,052, filed on Jul. 10, 2002, now abandoned.

(60) Provisional application No. 60/305,192, filed on Jul. 13, 2001.

(51) Int. Cl.
| C07K 16/38 | (2006.01) |
| C07K 17/06 | (2006.01) |
| C07D 213/55 | (2006.01) |
| C07D 401/02 | (2006.01) |
| C12N 5/20 | (2006.01) |
| G01N 33/533 | (2006.01) |

(52) U.S. Cl. .................. 530/388.9; 435/345; 436/544; 436/546; 546/278.7; 546/337; 530/389.8; 530/404; 530/405

(58) Field of Classification Search ................ 530/404, 530/405, 388.9, 389.8; 435/345; 436/544, 436/546; 546/278.7, 337
See application file for complete search history.

(56) References Cited

U.S. PATENT DOCUMENTS

| 5,302,715 A | 4/1994 | Buechler et al. |
| 6,087,383 A * | 7/2000 | Singh et al. ................ 514/357 |
| 2005/0244816 A1* | 11/2005 | Valdez ......................... 435/5 |

FOREIGN PATENT DOCUMENTS

| EP | 1207394 A2 | 2/2002 |
| FR | 2773994 | 7/1999 |
| WO | WO 95/23606 | 8/1995 |
| WO | WO 01/01135 A1 | 1/2001 |
| WO | WO 03/048386 | 6/2003 |
| WO | WO 03/075009 A1 | 9/2003 |

OTHER PUBLICATIONS

Akeb, F. et al., "Quantification of plasma and intracellular levels of the HIV protease inhibitor ritonavir by competitive ELISA," Journal of Immunologial Methods 263 (2002) 1-9.
Eaglings, V.A. et al., "CPY3A4-mediated hepatic metabolism of the HIV-1 protease inhibitor saquinavir in vitro," Xenobiotica, 2002. vol. 31, No. 1, 1-17.
Mansfeld, H-W et al., "Detection of inhibition of HIV-1 protease activity by an enzyme-linked immunosorbent assay (ELISA)," Journal of Immunological Methods, 161 (1993) 151-155.
Marzolini, C. et al., "Simultaneous determination of the HIV protease inhibitors indinavir, amprenavir, saquinavir, ritonavir, nelfinavir and the non-nucleoside reverse transcriptase inhibitor efavirenz by high-performance liquid chromatography after solid-phase extraction," Journal of Chromatography B, 740, (2000) 43-58.
Poirier, J-M et al., "Simultaneous Determination of the Five HIV-Protease Inhibitors: Amprenavir, Indinavir, Nelfinavir, Ritonavir, and Saquinavir in Human Plasma by Solid-Phase Extraction and Column Liquid Chromatography," Therapeutic Drug Monitoring, 22:465-473, 2000.
Remmel, R. et al., "Simultaneous HPLC Assay for Quantification of Indinavir, Nelfinavir, Ritonavir, and Saquinavir in Human Plasma," Clinical Chemistry, 46:1, 73-81 (2000).
Sarubbi, E. et al., "A high throughput assay for inhibitors of HIV-1 protease, Screening of microbial metabolites," FEBS 09419, vol. 279, No. 2, 265-269, (1991).
Valdez, H. et al., "Response to immunization with recall and neoantigens after prolonged administration of an HIV-1 protease inhibitor-containing regimen," AIDS, 2000, vol. 14, No. 1, 11-21.
Wiltshire, H.R. et al., "Chromatographic and Immunochemical Approaches to the Analysis of the HIV Protease Inhibitor Saquinavir in Plasma," Analytical Biochemistry, 281, 105-114 (2000).
Yu, S.-L. et al., "Assay of HIV-1 protease activity by use of crude preparations of enzyme and biotinlylated substrate," Journal of Virological Methods, 53 (1995) 63-73.

* cited by examiner

*Primary Examiner*—Mary E. Ceperley
(74) *Attorney, Agent, or Firm*—Marilyn L. Amick; Roche Diagnostics Operations, Inc.

(57) ABSTRACT

Activated haptens useful for generating immunogens to the HIV protease inhibitor atazanavir, immunogens useful for producing antibodies to atazanavir, and antibodies and labeled conjugates useful in immunoassays for determination of atazanavir. The haptens feature an activated functionality at the central, non-terminal hydroxyl group.

12 Claims, 2 Drawing Sheets

METHODS OF INHIBITING TRANSMISSION OF A COSTIMULATORY SIGNAL OF LYMPHOCYTES

RELATED APPLICATIONS

This application is a continuation-in-part of U.S. patent application Ser. No. 10/669,831 filed Sep. 24, 2003, which is a continuation-in-part of U.S. patent application Ser. No. 10/192,052 filed Jul. 10, 2002, now abandoned which claims priority to U.S. Provisional Application No. 60/305,192 filed Jul. 13, 2001.

FIELD OF THE INVENTION

This invention relates to protease inhibitor conjugates and antibodies useful in immunoassay methods for detecting protease inhibitors. More specifically, this invention relates to activated haptens useful for generating conjugates and derivatives of atazanavir, to immunogens useful for producing antibodies to atazanavir, and to antibodies and labeled conjugates useful in immunoassays for atazanavir.

BACKGROUND OF THE INVENTION

HIV protease inhibitors are an important new class of drugs which have made a significant impact on the health care of AIDS patients since the first one, saquinavir, was introduced to the marketplace in 1995. Examples of other protease inhibitors include amprenavir, indinavir, nelfinavir, lopinavir, ritonavir, and atazanavir. They are especially effective in combination with other anti-HIV drugs such as reverse transcriptase inhibitors or with other HIV protease inhibitors. In spite of remarkable success with these new therapeutic regimens, there are strong indications that results would be much improved if therapeutic drug testing methods were available for monitoring the concentrations of protease inhibitors. Not all patients respond optimally to protease inhibitor combination therapies. Even those who do respond can subsequently develop drug resistance due to the notoriously high rate of mutation of the HIV virus. However, it has been shown that there is a clear relationship between plasma levels of the protease inhibitors and therapeutic efficacy based upon decreased viral load and increased CD4 cell count. One problem lies in the fact that the drugs are metabolized extensively and are subject to complex drug-drug interactions. The results are extremely complex pharmacokinetics and a strong element of unpredictability between dosage and resultant drug levels at any particular time for any particular patient. With therapeutic drug monitoring, drug dosages could be individualized to the patient, and the chances of keeping the virus in check would be much higher. But routine therapeutic drug monitoring of protease inhibitors would require the availability of simple automated tests adaptable to high throughput clinical analyzers. Currently most reports on therapeutic drug monitoring of protease inhibitors have used HPLC methods which are slow, labor-intensive, and expensive. Recently there was a report of a radioimmunoassay (RIA) method for saquinavir (Wiltshire et al., Analytical Biochemistry 281, 105–114, 2000). However, such a method would not be adaptable to high-throughput therapeutic drug monitoring and, like all RIA methods, suffers from the disadvantages of having regulatory, safety and waste disposal issues related to the radioactive isotope label used in the assay. The most desirable assay formats for therapeutic drug monitoring are non-isotopic immunoassays, and such methods have heretofore been unknown for monitoring HIV protease inhibitors.

As indicated above, HPLC has been the method of choice for monitoring HIV protease inhibitors. Two recent reports in the literature describe HPLC assays for the simultaneous determination of several protease inhibitors in human plasma, Poirier et al., Therapeutic Drug Monitoring 22, 465–473, 2000 and Remmel et al., Clinical Chemistry 46, 73–81, 2000.

Chemical and biological assays generally involve contacting the analyte of interest with a pre-determined amount of one or more assay reagents, measuring one or more properties of a resulting product (the detection product), and correlating the measured value with the amount of analyte present in the original sample, typically by using a relationship determined from standard or calibration samples containing known amounts of analyte of interest in the range expected for the sample to be tested. Typically, the detection product incorporates one or more detectable labels which are provided by one or more assay reagents. Examples of commonly used labels include functionalized microparticles, radioactive isotope labels such as $^{125}I$ and $^{32}P$, enzymes such as peroxidase and beta-galactosidase and enzyme substrate labels, fluorescent labels such as fluoresceins and rhodamines, electron-spin resonance labels such as nitroxide free radicals, immunoreactive labels such as antibodies and antigens, labels which are one member of a binding pair such as biotin-avidin and biotin-streptavidin, and electrochemiluminescent labels such as those containing a ruthenium bipyridyl moiety. Sandwich assays typically involve forming a complex in which the analyte of interest is sandwiched between one assay reagent which is ultimately used for separation, e.g., antibody, antigen, or one member of a binding pair, and a second assay reagent which provides a detectable label. Competition assays typically involve a system in which both the analyte of interest and an analog of the analyte compete for a binding site on another reagent, e.g., an antibody, wherein one of the analyte, analog or binding reagent possesses a detectable label.

Copending U.S. patent application Ser. No. 09/712,525 filed Nov. 14, 2000 having the same assignee as the present application and published as EP 1 207 394 on May 22, 2002, describes a non-isotopic immunoassay for an HIV protease inhibitor comprising incubating a sample containing the inhibitor with a receptor specific for the inhibitor or for a metabolite of said inhibitor and further with a conjugate comprising an analog of the inhibitor and a non-isotopic signal generating moiety. Signal generated as a result of binding of the inhibitor by the receptor is measured and correlated with the presence or amount of protease inhibitor in the original sample. The protease inhibitor conjugates of the present invention are especially useful in such an assay.

Among other problems, there is a need for an antibody specific for atazanavir having essentially no cross-reactivity with the HIV protease inhibitors saquinavir, amprenavir, indinavir, nelfinavir, lopinavir, and ritonavir or with the atazanavir metabolite 4-pyridin-2-yl-benzoic acid.

SUMMARY OF THE INVENTION

It is against the above background that the present invention provides certain unobvious advantages and advance ments over the prior art. In particular, the inventors have recognized a need for improvements in atazanavir conjugates and antibodies useful in immunoassay.

The present invention provides activated haptens of atazanavir useful for generating immunogens, conjugates and antibodies to the HIV protease inhibitor atazanavir. These activated haptens have the general structure:

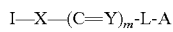

wherein I is an atazanavir radical, X is O or NH, Y is O, S or NH, m is 0 or 1, L is a linker consisting of from 0 to 40 carbon atoms arranged in a straight chain or a branched chain, saturated or unsaturated, and containing up to two ring structures and 0–20 heteroatoms, with the proviso that not more than two heteroatoms may be linked in sequence, and A is an activated functionality chosen from the group consisting of active esters, isocyanates, isothiocyanates, thiols, imidoesters, anhydrides, maleimides, thiolactones, diazonium groups and aldehydes.

The present invention also provides atazanavir immunogens having the structure:

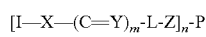

wherein I is an atazanavir radical, X is O or NH, Y is O, S, or NH, m is 0 or 1, L is a linker comprising 0 to 40 carbon atoms arranged in a straight chain or a branched chain, saturated or unsaturated, and further comprising up to two ring structures and 0–20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

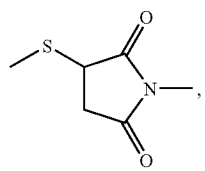

P is selected from the group consisting of polypeptides, polysaccharides and synthetic polymers, and n is a number from 1 to 50 per 50 kilodaltons molecular weight of P.

The present invention also provides labeled conjugates having the structure:

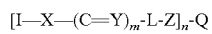

wherein I is an atazanavir radical, X is O or NH, Y is O, S, or NH, m is 0 or 1, L is a linker comprising 0 to 40 carbon atoms arranged in a straight chain or a branched chain, saturated or unsaturated, and further comprising up to two ring structures and 0–20 heteroatoms, with the proviso that not more than two heteroatoms are linked in sequence, Z is a moiety chosen from the group consisting of —CONH—, —NHCO—, —NHCONH—, —NHCSNH—, —OCONH—, —NHOCO—, —S—, —NH(C=NH)—, —N=N—, —NH—, and

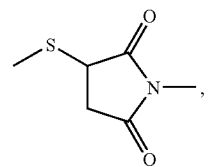

Q is selected from the group consisting of non-isotopic labels, and n is a number from 1 to 50 per 50 kilodaltons molecular weight of Q.

The present invention also provides antibodies to the HIV protease inhibitor atazanavir having less than 1% cross-reactivity to an HIV protease inhibitor selected from the group consisting of saquinavir, nelfinavir, indinavir, amprenavir, ritonavir, and lopinavir.

The present invention also provides antibodies to the HIV protease inhibitor atazanavir having less than 1% cross-reactivity to HIV protease inhibitors saquinavir, nelfinavir, indinavir, amprenavir, ritonavir, and lopinavir.

The present invention also provides antibodies to the HIV protease inhibitor atazanavir having less than 1% cross-reactivity to the atazanavir metabolite 4-pyridin-2-yl-benzoic acid.

Finally, the present invention provides antibodies generated from the immunogens of the invention as well as immunoassay methods and test kits which incorporate the antibodies and labeled conjugates of the present invention.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

DETAILED DESCRIPTION OF THE INVENTION

Figure 1:
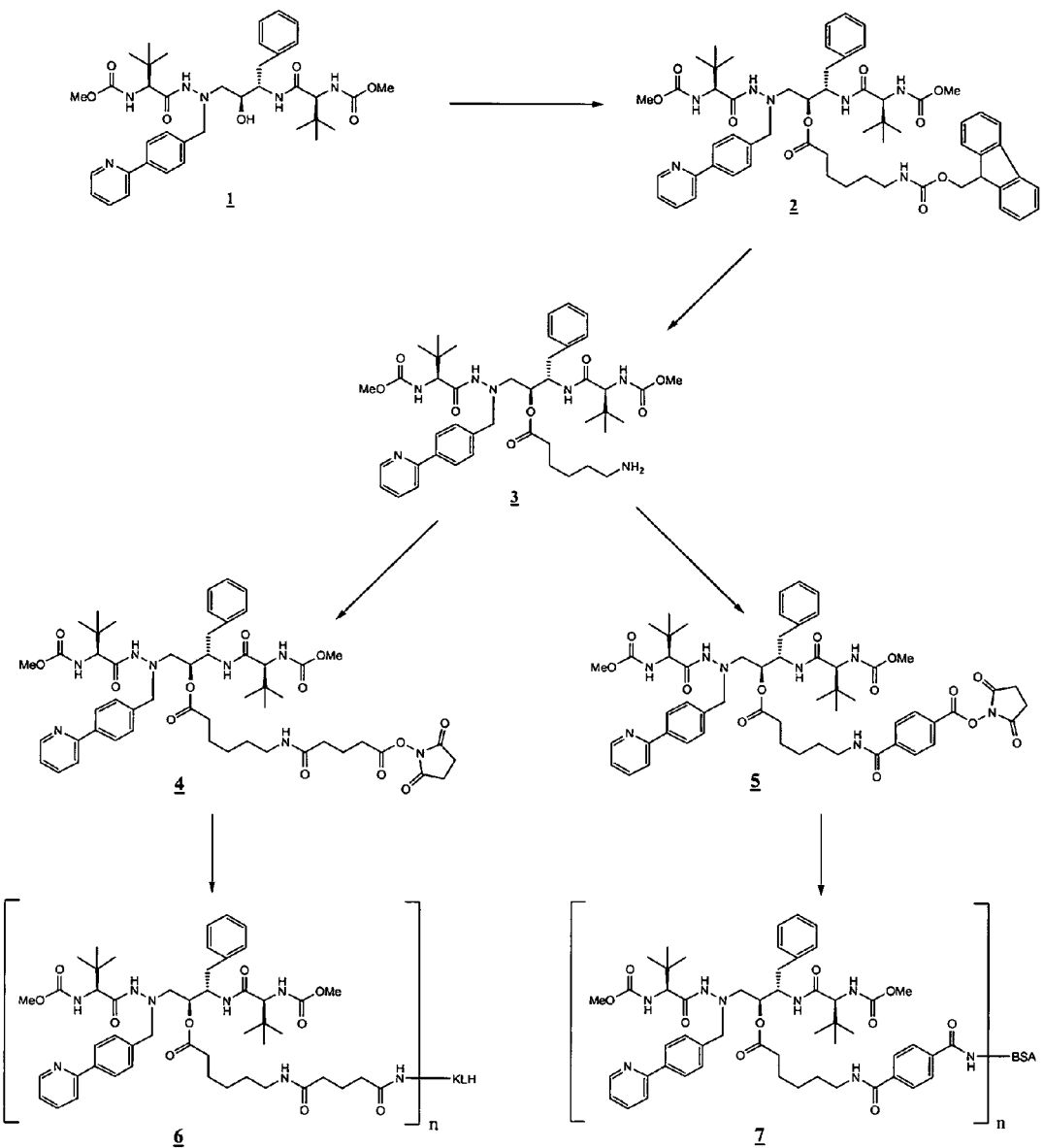
FIG. 1 illustrates a scheme for synthesis of O-acylated atazanavir activated haptens, KLH immunogen, and BSA conjugate.

In order that the invention may be more readily understood, reference is made to the following examples, which are intended to illustrate the invention, but not limit the scope thereof.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

As used herein, analyte refers to a substance, or group of substances, whose presence or amount thereof is to be determined.

Antibody means a specific binding partner of the analyte and is any substance, or group of substances, which has a specific binding affinity for the analyte to the essential exclusion of other unrelated substances. The term includes polyclonal antibodies, monoclonal antibodies and antibody fragments.

Haptens are partial or incomplete antigens. They are protein-free substances, mostly low molecular weight substances, which are not capable of stimulating antibody formation, but which do react with antibodies. The latter are formed by coupling a hapten to a high molecular weight carrier and injecting this coupled product into humans or animals. Examples of haptens include therapeutic drugs such as digoxin and theophylline, drugs of abuse such as morphine and LSD, antibiotics such as gentamicin and vancomycin, hormones such as estrogen and progesterone, vitamins such as vitamin B12 and folic acid, thyroxin, histamine, serotonin, adrenaline and others.

An activated hapten refers to a hapten derivative that has been provided with an available site for reaction, such as by the attachment of, or furnishing of, an activated group for synthesizing a derivative conjugate.

The term linker refers to a chemical moiety that connects a hapten to a carrier, immunogen, label, tracer or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen and sulfur. The use of a linker may or may not be advantageous or needed, depending on the specific hapten and carrier pairs.

A carrier, as the term is used herein, is an immunogenic substance, commonly a protein, which can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic as used herein refer to substances capable of producing or generating an immune response in an organism.

The terms conjugate and derivative refer to a chemical compound or molecule made from a parent compound or molecule by one or more chemical reactions.

As used herein, a detector molecule, label or tracer is an identifying tag which, when attached to a carrier substance or molecule, can be used to detect an analyte. A label may be attached to its carrier substance directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as $^{125}$I.

The term active ester within the sense of the present invention encompasses activated ester groups which can react with nucleophiles such as, but not limited to, free amino groups of peptides, polyaminoacids, polysaccharides or labels under such conditions that no interfering side reactions with other reactive groups of the nucleophile-carrying substance can usefully occur.

An object of the present invention is to provide activated atazanavir haptens that can be used to generate immunogens to atazanavir. These activated haptens are represented by the formula:

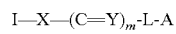

wherein I is an atazanavir radical, X is O or NH, Y is O, S or NH, m is 0 or 1, L is a linker consisting of from 0 to 40 carbon atoms arranged in a straight chain or a branched chain, saturated or unsaturated, and containing up to two ring structures and 0–20 heteroatoms, with the proviso that not more than two heteroatoms may be linked in sequence, and A is an activated functionality chosen from the group consisting of active esters, isocyanates, isothiocyanates, thiols, imidoesters, anhydrides, maleimides, thiolactones, diazonium groups and aldehydes.

As used herein, an HIV protease inhibitor radical is the intact drug lacking only a hydroxyl group or an amino group, XH, where X is O or NH. The X and C=Y moieties include, but are not limited to, esters (where X is O, Y is O, and m is 1), amides (where X is NH, Y is O, and m is 1), urethanes (where X is O, Y is O, m is 1, and the first atom in L adjacent to C=Y is N), ureas (where X is NH, Y is O, m is 1, and the first atom in L adjacent to C=Y is N), thioureas (where X is NH, Y is S, m is 1, and the first atom in L adjacent to C=Y is N), amidines (where X is NH, Y is NH, and m is 1), ethers (where X is O, and m is 0) and amines (where X is NR wherein R is H or lower alkyl, and m is 0). "Lower alkyl" means methyl, ethyl, propyl and isopropyl groups. Preferred activated haptens are esters or urethanes formed with the central, non-terminal hydroxyl group common to all HIV protease inhibitors. This central hydroxyl group is functionally important for the therapeutic activity of the protease inhibitors but also provides a convenient handle for derivatization and linker attachment. Moreover, generally the metabolism of the protease inhibitors takes place at terminal residues, and therefore the central hydroxyl groups are attractive sites for immunogens designed to generate antibodies which discriminate between parent drug and metabolites. As used herein, this central hydroxyl group is designated as HO$^c$. When the hydrogen of the central hydroxyl group is replaced by a (C=Y)$_m$-L-A group, the residual bonded oxygen is shown as O$^c$.

The linker L serves the purpose of providing an additional spacer between the terminal activated functionality A and the HIV protease inhibitor radical, the first spacer being the X and C=Y groups. Linker length and composition are well known to those skilled in the art to have important effects on immunogen response and conjugate performance. There are many examples of commercially available or easily synthesized linkers in the literature for attachment to hydroxyl and amino groups. For a good treatise on this subject, the reader is referred to *Bioconjugate Techniques*, G. Hermanson, Academic Press, 1996. In some cases the additional linker L is dispensed with and the C=Y moiety is directly attached to an activated functionality A. An example of a preferred linker moiety L is —(CH$_2$)$_n$—NH— where x is 1–12. Particularly preferred is x=5 in combination with C=Y where Y is O (i.e., aminocaproyl esters). Such linkers are formed by acylation of an HIV protease inhibitor with an N-protected amino acid (i.e., aminocaproic acid). The protecting group is preferably one which is removed under mildly basic or acidic conditions so as not to affect the integrity of the X—C=Y bonds or other moieties in the HIV protease inhibitor radical. An example of an N-protecting group removed under mildly basic conditions is fluorenylmethyloxycarbonyl (FMOC). An example of an N-protecting group easily removed with acid is t-butyloxycarbonyl (BOC). Many other suitable N-protecting groups are well known in the art (see "Protective Groups" in *Organic Synthesis,* 2nd edition, T. Greene and P. Wuts, Wiley-Interscience, 1991).

The acylation reaction of HIV protease inhibitor hydroxyl or amino groups with N-protected amino acids is accomplished by using condensation reagents such as carbodiimides with or without a catalyst. A preferred combination is dicyclohexylcarbodiimide with dimethylaminopyridine as catalyst. The acylation reaction is carried out in a suitable solvent such as methylene chloride at 0–35° C. for a time which typically ranges from 0.5 to 7 days. Following isolation of the product, the N-protecting group is removed. For the preferred FMOC protecting group, this is accomplished by treatment with a solution of 10% piperidine in methylene chloride for 0.5 to 2 hours. The amino group of the resultant aminoacyl-protease inhibitor is amenable to acylation reactions with a wide variety of carboxyl activated linker extensions or labels which are well known to those skilled in the art to which the present invention belongs. Linker extension is often performed at this stage to generate terminal activated groups A such as active esters, isocyanates and maleimides. For example, reaction of the aminoacyl-protease inhibitor with one end of homobifunctional N-hydroxysuccinimide esters of bis-carboxylic acids such as terephthalic acid will generate stable N-hydroxysuccinimide ester terminated linker adducts which are useful for conjugation to amines on polypeptides, polysaccharides, and labels. Linker extension can also be accomplished with heterobifunctional reagents such as maleimido alkanoic acid N-hydroxysuccinimide esters to generate terminal maleimido groups for subsequent conjugation to thiol groups on polypeptides and labels. Alternatively, an amino-terminated linker can be extended with a heterobifunctional thiolating reagent which reacts to form an amide bond at one end and a free or protected thiol at the other end. Some examples of thiolating reagents of this type which are well known in the art are 2-iminothiolane (2-IT), succinimidyl acetylthiopropionate (SATP) and succinimido 2-pyridyldithiopropionate (SPDP). The incipient thiol group is then available, after deprotection, to form thiol ethers with maleimido or bromoacetylated modified immunogens or labels. Yet another alternative is to convert the amino group of the amino-terminated linker into a diazonium group and hence the substance into a diazonium salt, for example, by reaction with an alkali metal nitrite in the presence of acid, which is then reactive with a suitable nucleophilic moiety, such as, but not limited to, the tyrosine residues of peptides, proteins, polyaminoacids and the like. Examples of suitable amino-terminated linkers for conversion to such diazonium salts include aromatic amines (anilines), but may also include the aminocaproates and similar substances referred to above. Such anilines may be obtained by substituting into the coupling reaction between the hydroxyl of a protease inhibitor and an N-protected amino acid, as discussed above, the corresponding amino acid wherein the amino group is comprised of an aromatic amine, that is, an aniline, with the amine suitably protected, for example, as an N-acetyl or N-trifluoroacetyl group, which is then deprotected using methods well-known in the art. Other suitable amine precursors to diazonium salts will be suggested to one skilled in the art of organic synthesis.

Another favored type of heterobifunctional linker is a mixed active ester/acid chloride such as succinimido-oxycarbonyl-butyryl chloride. The more reactive acid chloride end of the linker preferentially acylates amino or hydroxyl groups on the HIV protease inhibitor to give N-hydroxysuccinimidyl ester linker adducts directly.

Yet another type of terminal activated group useful in the present invention is an aldehyde group. Aldehyde groups may be generated by coupling the hydroxyl of the protease inhibitor with an alkyl or aryl acid substituted at the omega position (the distal end) with a masked aldehyde group such as an acetal group, such as 1,3-dioxolan-2-yl or 1,3-dioxan-2-yl moieties, in a manner similar to that described previously, followed by unmasking of the group using methods well-known in the art. (See, e.g., T. Greene and P. Wuts, supra). Alternatively, alkyl or aryl carboxylic acids substituted at the omega position with a protected hydroxy, such as, for example, an acetoxy moiety, may be used in the coupling reaction, followed by deprotection of the hydroxy and mild oxidation with a reagent such as pyridinium dichromate in a suitable solvent, preferably methylene chloride, to give the corresponding aldehyde. Other methods of generating aldehyde-terminated substances will be apparent to those skilled in the art.

In certain cases, it is desirable to introduce polarity into the linker composition to improve solubility or performance characteristics in the assay of interest. Particularly useful in this regard are peptide linkers, which offer a wide diversity of possibilities for optimization and are readily accessible by solid phase peptide synthesis or by other means.

Another approach which is particularly useful for generating acylated HIV protease inhibitors with urethane, urea or thiourea bonds at the point of attachment to the protease inhibitor is to react the hydroxyl or amino group of the protease inhibitor with a linker isocyanate or a linker isothiocyanate. For example, a carboxyalkylisocyanate with or without a protecting group on the carboxyl group may be reacted directly with the target hydroxyl group on a protease inhibitor to give a protected carboxyalkylurethane or a carboxyarylurethane. The protected carboxy is preferably an ester which is removed under basic or acidic conditions. Once freed, the carboxyl group may be activated to give an active ester for subsequent conjugation or which may be directly conjugated to polypeptides, polysaccharides and labels. Alternatively, a preactivated carboxyalkylisocyanate or carboxyarylisocyanate such as N-hydroxysuccinimidyl-isocyanatobenzoate may be reacted directly with protease inhibitor hydroxyl or amine groups to give linker-acylated protease inhibitor with an active ester terminus.

Yet another approach for generating urethane, urea and thiourea bonds at the point of attachment to the HIV protease inhibitor is to first treat the target hydroxyl or amine function with phosgene or thiophosgene to give an oxycarbonyl chloride or oxythiocarbonyl chloride. The latter intermediates react readily with amines to give urethanes, ureas or thioureas. Alternative phosgene equivalents such as carbonyldiimidazole or disuccinimidyl-carbonate will react similarly.

Another approach is also useful for generating alkylated derivatives of HIV protease inhibitors out of the central hydroxyl group. For example, a protease inhibitor (or properly protected protease inhibitor) can be reacted with a strong base under suitable conditions to deprotonate the central hydroxyl group. This can be reacted with a variety of halo alkyl reagents bearing a protected carboxylic acid or appropriately protected functionality such as an amino group protected as the phthalimide to form ether linkages. The protected carboxyl group is preferably an ester which is removed under acid or basic conditions. The free carboxylic acid group may be activated to give an active ester for subsequent conjugation to polypeptides, polysaccharides and labeling groups. The free amino group, after deprotection, can also be extended using a bi-functional linker with an activated carboxylic acid group or it can be coupled to a polypeptide by means of a urea linkage or similar group.

For generation of amidine adducts, the amine of an HIV protease inhibitor is reacted with an imidoester, many of which are known in bioconjugate chemistry as linkers (see Hermanson, ibid.)

Alternatively, protease inhibitors derivatized with linkers bearing an imidate moiety (imido ester; or iminium group) as the activated group may be obtained by, for example, using a linker carrying a suitable precursor group, for example, a terminal nitrile group, when appropriately functionalizing a protease inhibitor. For example, an $O^c$-alkylated derivative, or an $O^{ar}$-alkyl derivative, for example, of nelfinavir, or $N^{ar}$-alkyl derivative, for example, of amprenavir, carrying a terminal nitrile may be synthesized in a manner analogous to that described above, followed by conversion of the nitrile to an imidate group by methods known in the art, for example, by treatment with hydrogen chloride in an alcohol. See also: Hermanson, ibid; and Jerry March, *Advanced Organic Chemistry*, $3^{rd}$ Ed., John Wiley & Sons, 1985. Other methods of obtaining imido esters will be suggested to one skilled in the art.

In certain protease inhibitors with multiple hydroxy groups, i.e., indinavir and nelfinavir, or hydroxy groups and amino groups in the same protease inhibitor, i.e., amprenavir, it may be necessary to protect one of the groups in order to effect clean reaction at the other functional group. For example, the indinavir indane hydroxyl group can be protected with an isopropylidine group bridging to the adjacent amide nitrogen. For the purposes of this application the indane hydroxyl group is labeled as $HO^{in}$ to distinguish it from $HO^c$. The isopropylidine protected indinavir $HO^{in}$ by extension is designated as $O^{in}N^{in}$-isopropylidinyl.

In another example, nelfinavir aromatic hydroxyl ($HO^{ar}$ as used herein) is protected with a t-butyldimethylsilyl (TBDMS) group before reaction with the central hydroxyl group, $HO^c$. Many other suitable protecting groups for alcohols and phenols are known in the art, and the reader is again referred to Greene and Wuts for further examples.

In other cases, adjustment of the reaction conditions will allow for selection of one functional group over another, and protection will not be needed. An example of the latter approach is the selective acylation of amprenavir hydroxyl group or amino group. Another example is the selective alkylation of nelfinavir phenolic hydroxyl group ($HO^{ar}$) in the presence of unprotected aliphatic central hydroxyl group.

From the description above, it is evident that there are many variations of linker technology which will provide an activated terminal group A in the HIV protease inhibitor hapten compositions of interest. Some of these variations will now be described in more detail. Active esters are the most preferred A group. Active esters of the invention are reactive with nucleophiles, especially primary amines, at relatively low temperatures, generally 0–100° C. in a variety of aqueous and non-aqueous solvent mixtures. Typical conditions for active ester couplings with primary or secondary amines to give amides are reaction in dipolar aprotic solvents such as N,N-dimethylformamide (DMF) or dimethylsulfoxide (DMSO) with or without added water at room temperature. A buffer or a tertiary amine is often added to maintain the basic pH needed to keep the primary amine reactant in a deprotonated state. Typical active esters are p-nitrophenyl esters, N-hydroxysulfosuccinimidyl esters, N-hydroxysuccinimidyl esters, 1-hydroxybenzotriazolyl esters and pentafluorophenyl esters. Especially preferred are the N-hydroxysuccinimidyl esters because of their balance of stability, reactivity and the easy removal of side product N-hydroxysuccinimide. Other active esters are well known to those skilled in the art and may be used similarly.

An alternative activation method for protease inhibitor linkers terminated with carboxylic acids is in situ preparation of anhydrides. Particularly preferred are the mixed carbonic anhydrides formed with alkylchloroformates such as isobutylchloroformate. These mixed anhydrides are readily formed at temperatures typically ranging from −30° C. to +30° C., usually −20° C. to 0° C., by the reaction of carboxylic acid and alkylchloroformate in the presence of a tertiary amine such as triethylamine or N-methylmorpholine in solvents such as DMF or tetrahydrofuran (THF) for 5 minutes to 1 hour. The mixed anhydride is then reacted with amino groups on labels, immunogens and carriers, typically for 5 minutes to 1 hour at 0° C. to +30° C. to give stable amide conjugates. Also, symmetrical anhydrides may be formed by reaction of two equivalents of a protease inhibitor linker carboxylic acid group with carbodiimides such as dicyclohexylcarbodiimides (DCC) or ethyl-dimethylamino-propyl-carbodiimide (EDAC) in a variety of solvents such as THF, DMF or dichloromethane. The activation and coupling to amines is typically carried out under similar conditions as the mixed anhydride coupling above.

Yet another activation method for protease inhibitor linkers terminated with carboxylic acids is conversion to masked thiol groups, such as thiolactones, by coupling of the carboxylic acid group with a substance such as homocysteine thiolactone. (See, e.g., U.S. Pat. No. 5,302,715.) The resulting linker-thiolactone may then be unmasked with mild base to give a terminal thiol which is then reactive with moieties like maleimido groups or bromoacetyl or iodoacetyl groups, such as on maleimido- or haloacetyl-modified peptides, polysaccharides, polyaminoacids, labels and the like, to give thio-maleimido or thio-acetyl adducts in a similar manner to that described previously.

Other useful A groups are isothiocyanate or isocyanate moieties. Isothiocyanates also react readily with nucleophiles such as primary amines to give thioureas under conditions similar to the active ester reaction described above, while isocyanates react similarly to give ureas. An added advantage of the isothiocyanate or isocyanate reaction is that it is an addition rather than a substitution, and therefore there is no side-product to be concerned about as in the case of active esters. Isocyanate equivalents, such as, for example, p-nitrophenyloxycarbonylamino moieties react similarly with primary amines to give ureas.

Finally, when the target nucleophile is a thiol group, maleimides are especially preferred because of their rapid formation of thiol ethers under very mild conditions, i.e., ambient temperature and neutral pH. Alternatively, active haloalkyl A groups such as iodoacetyl or bromoacetyl also react readily to form stable thiol ethers.

Another object of the invention is to provide immunogens with the structure:

$$[I—X—(C=Y)_m\text{-}L\text{-}Z]_n\text{-}P$$

wherein I is an atazanavir radical, X is O or NH, Y is O, S, or NH, m is 0 or 1, L is a linker comprising 0 to 40 carbon atoms arranged in a straight chain or a branched chain, saturated or unsaturated, and further comprising up to two ring structures and 0–20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

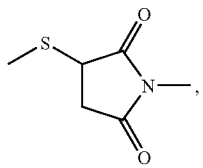

P is selected from the group consisting of polypeptides, polysaccharides and synthetic polymers, and n is a number from 1 to 50 per 50 kilodaltons molecular weight of P.

For immunogens, the preferred mode of the invention is to link from the central hydroxyl group common to all HIV protease inhibitors by an acylation reaction to form an ester bond (i.e., X is O, m is 1 and Y is O). A wide variety of linkers L and activated functionalities A may be used as described above. Thus an activated hapten of the type I—X—(C=Y)m-L-A is constructed and reacted with an immunogenic carrier substance. The immunogenic carrier is typically a polypeptide or a polysaccharide with a molecular weight more than 10 kD. Preferred immunogenic carriers are polypeptides with a molecular weight more than 100 kD. Examples of preferred carrier substances are keyhole limpet hemocyanin (KLH), *Limulus polyphemus* hemocyanin (LPH) and bovine thyroglobulin (BTG). The reaction between the activated hapten and amino groups on the carrier is typically carried out in a buffered mixture of water and a water miscible organic solvent such as DMSO at room temperature for 0.5 to 5 days. The pH of the buffer is typically between 6 and 8 for active esters, isocyanates, and isothiocyanates, or between 7 and 10 for imidates, and is adjusted according to the known reactivity of the carrier amino groups and the activated functionality. In the case where the terminal group A is a maleimide, the reactive groups on the carrier are thiols. These thiol groups are either native to the carrier or may be introduced using thiolating reagents such as 2-IT or SATP. The optimum pH for the conjugation of maleimides to thiol groups to give thioethers is typically between 5 and 7. Following the reaction, the immunogen is dialyzed or subjected to size exclusion chromatography in order to remove unconjugated hapten and organic solvent.

An alternative method of obtaining immunogens is to react an activated hapten wherein A is aldehyde with the amino groups of a carrier protein or polypeptide to form a Schiff base, followed by reduction with mild reducing agents such as a cyanoborohydride, to form a stable amine bond. Variations on this last approach will also be suggested to those skilled in the art to which the present invention belongs.

Yet another object of the present invention is to provide antibodies to HIV protease inhibitors generated from the immunogens of the invention. In order to generate antibodies, the immunogen can be prepared for injection into a host animal by rehydrating lyophilized immunogen to form a solution or suspension of the immunogen. Alternatively, the immunogen may be used as a previously prepared liquid solution or as a suspension in buffer. The immunogen solution is then combined with an adjuvant such as Freund's to form an immunogen mixture. The immunogen may be administered in a variety of sites, at several doses, one or more times, over many weeks.

Preparation of polyclonal antibodies using the immunogens of the invention may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hybridizing mouse lymphocytes, from mice immunized as described above, and myeloma cells using a polyethylene glycol method such as the technique described in *Methods in Enzymology* 73 (*Part B*), pp. 3–46, 1981.

In the case of ELISA assays, protease inhibitor derivatives coupled to bovine serum albumin (BSA) are preferred for coating of microtiter plates.

Another object of the invention is to provide labeled conjugates with the structure:

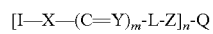

[I—X—(C=Y)$_m$-L-Z]$_n$-Q wherein I is an atazanavir radical, X is O or NH, Y is O, S, or NH, m is 0 or 1, L is a linker comprising 0 to 40 carbon atoms arranged in a straight chain or a branched chain, saturated or unsaturated, and further comprising up to two ring structures and 0–20 heteroatoms, with the proviso that not more than two heteroatoms are linked in sequence, Z is a moiety chosen from the group consisting of —CONH—, —NHCO—, —NHCONH—, —NHCSNH—, —OCONH—, —NHOCO—, —S—, —NH(C=NH)—, —N=N—, —NH—, and

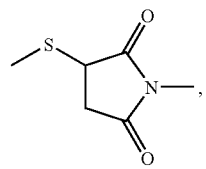

Q is selected from the group consisting of non-isotopic labels, and n is a number from 1 to 50 per 50 kilodaltons molecular weight of Q.

For the synthesis of conjugates of HIV protease inhibitors and non-isotopic labels, similar procedures as for the preparation of immunogens are employed.

Alternatively, the activated haptens may be conjugated to amino or thiol groups on enzymes to prepare labels for ELISA application. Some examples of useful enzymes for ELISA for which conjugates are well-known in the art are horseradish peroxidase (HRP), alkaline phosphatase and β-galactosidase. Conjugates of proteins including enzymes are typically prepared in a buffered mixture of water and water miscible organic solvents followed by dialysis analogous to the conditions for preparation of immunogens. In the case of latex agglutination assays, conjugates with aminated dextran carriers having molecular weights between 10 kD and 300 kD, preferably 40 kD, are especially useful. These conjugates are prepared in buffered solvent mixtures as above or in an anhydrous organic solvent such as DMSO containing a tertiary amine such as triethylamine to promote the reaction. In the case of labels of small molecular weight, i.e., less than 1 kD, reaction conditions are adjusted according to the nature of the label. One label which is particularly preferred is biotin in combination with labeled avidin or streptavidin. The versatility of (strept)avidin/biotin systems for non-isotopic detection is well known in the art of bio-conjugate chemistry (see Hermanson, ibid.). A variety of enzyme- and fluorophore-labeled conjugates of avidin and streptavidin are commercially available to detect biotin-labeled substances in a high affinity interaction. Furthermore, a variety of biotinylating agents are commercially available to react with activated functionalities A. For example, a biotin-amine derivative may be reacted with activated haptens of the invention in which A is an active ester, isocyanate or isothiocyanate to give biotin amide, urea and thiourea conjugates respectively. These coupling reactions are typically carried out in a dipolar aprotic solvent such as DMF or DMSO containing an organic base such as triethylamine at room temperature for 0.5 to 5 days. The biotin conjugates are preferentially isolated by chromatographic methods such as reversed phase HPLC.

Other preferred labels are fluorophores such as fluorescein, rhodamine, TEXAS RED fluorescent dye (Molecular Probes, Inc.), dansyl, and cyanine dyes, e.g., Cy-5, of which many activated derivatives are commercially available. Generally, these conjugates may be prepared similarly as biotin conjugates in a dipolar aprotic solvent containing a tertiary amine followed by chromatographic isolation.

It is also possible to use a reporter group as label which is indirectly coupled to a detection system. One example is biotin as described above. Another example is mycophenolic acid derivatives for inhibition of inosine monophosphate dehydrogenase as described in PCT publication WO 200101135, published Jan. 4, 2001.

It will be obvious to those skilled in the art that there are other possibilities for non-isotopic labels including electrochemiluminescent labels such as ruthenium bipyridyl derivatives, chemiluminescent labels such as acridinium esters, electrochemical mediators, and a variety of microparticles and nanoparticles which can be used for the invention after suitable introduction of suitable nucleophilic groups on the label, e.g., amines or thiols, for reaction with activated groups A on the HIV protease inhibitor activated hapten.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

Specific Embodiments

In the examples that follow, numbers in boldface type refer to the corresponding structure shown in the drawings. These examples are presented for illustration only without any intent to limit the invention.

O-Acylation of Atazanavir

EXAMPLE 1

Synthesis of $O^c$—(N-FMOC-aminocaproyl)-atazanavir (2)

$O^c$-(N-FMOC-aminocaproyl)-atazanavir (2) was prepared by stirring atazanavir (1, 0.20 g), FMOC-aminocaproic acid (0.010 g, 1 eq), DCC (0.059 g, 1 eq), and DMAP (0.038 g, 1 eq) were stirred overnight in anhydrous methylene chloride (40 mL) at room temperature. Following this, an additional 0.5 eq of FMOC-aminocaproic acid and 0.5 eq of DCC were added, and stirring continued for a further 3 days. The mixture was filtered, and the filtrate was evaporated to dryness under reduced pressure and directly purified by silica gel chromatography under a positive pressure of nitrogen (3% methanol in chloroform elution) to give the product $O^c$-(N-FMOC-aminocaproyl)-atazanavir (7A, 210 mg; 71%) as a white solid. M+H 1040.5.

Deprotection of O-acylated Atazanavir

EXAMPLE 2

Synthesis of $O^c$-(aminocaproyl)-atazanavir (3)

$O^c$-(N-FMOC-aminocaproyl)-atazanavir (2) from Example 1 (0.092 g) was stirred 1 hour in 10% piperidine in anhydrous methylene chloride (4 mL) at room temperature. The mixture was evaporated to dryness under reduced pressure. Two silica gel chromatography purifications were performed, the first column using 40% methanol in ethyl acetate (EtOAc) and the second column using 20% methanol in EtOAc to give the product $O^c$-(aminocaproyl)-atazanavir 3 as a solid (0.070 g, 97%). M+H 818.4.

In another run, 3 was isolated as the trifluoroacetic acid (TFA) salt after purification by preparative RP-HPLC (C18, gradient of 5% to 100% of 0.1% TFA-acetonitrile in 0.1% TFA-water).

Linker Extension of O-Acylated Atazanavir to Generate Activated Haptens

EXAMPLE 3

Synthesis of $O^c$-(succinimido-oxycarbonyl-butyryl-aminocaproyl)-atazanavir (4)

$O^c$-(aminocaproyl)-atazanavir (3) as the TFA salt (0.070 g), triethylamine (22 μL), and succinimido-oxycarbonyl butyryl chloride (0.0195 g) were stirred for 3 hours in dry THF at about 0° C. (ice-water bath). The reaction was evaporated to dryness, redissolved in 15% THF in ethyl acetate, and purified by silica gel chromatography (elution with 30% THF in EtOAc, column pre-washed with several column volumes of 15% THF in EtOAc). Fractions containing product were combined, evaporated, redissolved in dry methylene chloride ($CH_2C_{12}$) and re-evaporated (repeated several times) to yield $O^c$-(succinimido-oxycarbonyl-butyryl-aminocaproyl)-atazanavir (4) as a solid (24 mg, 31%). M+H 1029.4.

EXAMPLE 4

Synthesis of $O^c$-[4'-(succinimido-oxycarbonyl)-benzoyl-aminocaproyl]-atazanavir (5)

A solution of $O^c$-(aminocaproyl)-atazanavir (3, 0.054 g) in 2 mL of dry DMF was added slowly to a stirring, cooled solution (ice-water bath) of disuccinimidyl terephthalate (0.0228 g) in 4.5 mL of dry DMF. After brief stirring, triethylamine (50 µL) was added and the reaction stirred overnight. Analysis by HPLC indicated essential completion of the reaction. Solvent was removed on a rotovap under high vacuum (at less than 25° C.), the residue redissolved in acetonitrile-water and purified by preparative RP-HPLC (C18, gradient of 5% to 100% of 0.1% TFA-acetonitrile in 0.1% TFA-water) to give, from the main peak after evaporation of acetonitrile, freezing and lyophilization, the product $O^c$-[4'-(succinimido-oxycarbonyl)-benzoyl-aminocaproyl]-atazanavir (5), assigned as the trifluoroacetic acid salt, in two cuts (0.036 g and 0.007 g, combined 0.043 g, 55%). M+H 1063.5 (free base).

Conjugation of Atazanavir to Proteins

EXAMPLE 5

Synthesis of $O^c$-(succinimido-oxycarbonyl-butyryl-aminocaproyl)-atazanavir conjugate with KLH (6)

$O^c$-(succinimido-oxycarbonyl-butyryl-aminocaproyl)-atazanavir KLH conjugate was prepared from purified keyhole limpet hemocyanin (60 mg) and $O^c$-(succinimido-oxycarbonyl-butyryl-aminocaproyl)-atazanavir (4) from Example 3 (17 mg). The keyhole limpet hemocyanin and $O^c$-(succinimido-oxycarbonyl-butyryl-aminocaproyl)-atazanavir were stirred 2 days in 40% DMSO in 50 mM potassium phosphate, pH 7.5 (1.5 mL), at room temperature. The mixture was sequentially dialyzed against 30%, 20%, 10% and 0% DMSO in 1 liter 50 mM potassium phosphate, pH 7.5, at room temperature, followed by dialysis against 1 liter 50 mM potassium phosphate, pH 7.5, at 4° C. Protein quantification of the retentate by Coomassie Blue Protein Assay showed 10.8 mg/mL, 92% protein recovery (KLH standard/control). Amine quantification by TNBS colorimetric assay showed 56% lysine modification.

EXAMPLE 6

Synthesis of $O^c$-[4'-(succinimido-oxycarbonyl)-benzoyl-aminocaproyl]-atazanavir Conjugate with BSA (7)

$O^c$-[4'-(succinimido-oxycarbonyl)-benzoyl-aminocaproyl]-atazanavir BSA conjugate was prepared from bovine serum albumin (100 mg) and $O^c$-[4'-(succinimido-oxycarbonyl)-benzoyl-aminocaproyl]-atazanavir (5) as the TFA salt, from Example 4 (3 mg). The bovine serum albumin and $O^c$-[4'-(succinimido-oxycarbonyl)-benzoyl-aminocaproyl]-atazanavir were stirred 2 days in 40% DMSO in 50 mM potassium phosphate, pH 7.5 (1.5 mL), at room temperature. The mixture was sequentially dialyzed against 30%, 20%, 10% and 0% DMSO in 1 liter 50 mM potassium phosphate, pH 7.5, at room temperature, followed by dialysis against 1 liter 50 mM potassium phosphate, pH 7.5, at 4° C. Protein quantification by Coomassie Blue protein assay showed quantitative recovery of protein at 10.0 mg/mL (BSA standard/control). UV difference spectroscopy showed the ratio of hapten to BSA to be 1:1.7.

Development of Antibodies to Atazanavir

EXAMPLE 7

Immunization and Fusion

Female Balb/c mice 8 weeks of age were immunized with 100 µg of KLH immunogen 6 emulsified in Complete Freund's adjuvant via intraperitoneal injection. Twenty-one days later, another immunization of the same dose followed in Incomplete Freund's adjuvant. Four further injections were carried out using the same dosage and alternating with Ribi adjuvant at approximately 21-day intervals. All adjuvants were from Sigma Chemical Co.

The mouse selected for fusion was killed via exsanguination. The spleen was harvested and ground between two sterile glass slides to release the lymphocytes. The resulting lymphocyte suspension was used to fuse with the F0 myeloma cell line (ATCC CRL 1646).

Fusion consisted of adding myeloma cells (⅕ the number of lymphocytes) to the lymphocytes, washing via centrifugation, resuspension in serum-free warm Iscove's modified Dulbecco's media (IMDM), and re-centrifugation. The centrifuge tubes containing the resulting pellets were gently tapped to loosen the cells, then 1 mL of warmed PEG/DMSO solution (Sigma Chemicals) was slowly added with gentle mixing. The cells were kept warm for 1.5 minutes, after which pre-warmed serum-free IMDM was added at the following rates: 1 ml/min, 2 ml/min, 4 ml/min, and 10 ml/min. Then the tube was filled to 50 ml, sealed, and incubated for 15 minutes. The cell suspensions were centrifuged, the supernatant decanted, and IMDM containing 10% fetal calf serum was added. The cells were centrifuged once again and resuspended in complete cloning medium. This consisted of IMDM, 10% FCS, 10% Condimed H1 (Roche Molecular Systems), 4 mM Glutamine, 50 µM 2-mercaptoethanol, 40 µM ethanolamine, pen/strep antibiotics. The cells were suspended at a density of $4 \times 10^5$ lymphocytes/ml, distributed 100 µL/well into sterile 96-well sterile microculture plates and incubated at 37° C. in 5% $CO_2$ for 24 hours. The next day, 100 µL of hypoxanthine-methotrexate-thymidine (HMT) selective medium (cloning medium+1:25 HMT supplement from Sigma Chemicals) was added. On the $6^{th}$ day of incubation, approximately 150 µL of media was drawn from each well using a sterile 8-place manifold connected to a light vacuum source. One hundred fifty microliters of hypoxanthine-thymidine (HT) media was then added. This consisted of cloning medium+1:50 HT supplement (Sigma Chemicals). The plates were returned to the incubator and inspected daily for signs of growth. When growth was judged sufficient, wells were screened for antibody production via ELISA.

EXAMPLE 8

Antibody Screening

Screening of growing hybridomas was carried out by an ELISA using the atazanavir-BSA conjugate (7) and free atazanavir. Microplates were coated with 50 µL atazanavir-BSA conjugate at 1 µg/mL in 0.1 M carbonate buffer, pH 9.5 for 1 hour at 37° C. (humidified). The plates were then emptied and filled with a post-coat solution consisting of Tris buffer, 1% gelatin hydrolysate, 2% sucrose, and 0/17%

TWEEN 20 (all from Sigma Chemical Co.). The plates were incubated for an additional 1 hour at 37° C. (humidified) after which they were washed with phosphate-buffered saline containing 0.1% TWEEN 20. The plates were then filled with a 2% sucrose solution in 0.15 M Tris, pH 7.2–7.4 briefly, then emptied and allowed to air dry at room temperature. When dried, the plates were packed in zip-lock bags containing several desiccant pillows, sealed, and stored at 4° C. until use.

When the growing clones were judged ready for testing, 25 μL of supernatant from the wells were taken and transferred to 96-well flexible plates. Culture medium was added to each well to provide a 1:10 dilution of the media sample. Two atazanavir-BSA coated wells were used for each culture well tested. One well received 25 μL of PBS buffer, the other received 25 μL of PBS containing atazanavir drug at a concentration of 800 ng/ml. Twenty-five microliters of the diluted sample were transferred to each of two of the coated wells above. The plates were incubated covered for 1 hour at 37° C., then washed with PBS-TWEEN. The wells were then filled with 100 μL of goat anti-mouse IgG-HRP conjugate (Zymed Labs) diluted 1:5,000 in PBS-TWEEN and the plates re-incubated for 1 hour. The plates were then washed again, and 100 μL of K-BLUE SUBSTRATE (Neogen Corp) were added to each well. This was allowed to develop for 5–15 minutes, the reaction being stopped by the addition of 100 μL of 1 N HCl. Color was read via a microplate reader at 450 nm and collected by computer for analysis. Criteria for selection were binding to the well in which the PBS was added and significant inhibition of binding in the well receiving the free drug.

TABLE 1

Representative portion of the screening of the plates

| Culture well/clone | OD in absence of free drug | OD in presence of free drug |
|---|---|---|
| 39-G2 (ATZ 3) | 3.602 | 2.001 |
| 56-G4 (ATZ 4) | 1.499 | 0.992 |

Subsequent to the selection of a clone from the fusion culture plates, the cells were subjected to stringent cloning via limiting dilution. Subclones growing from those wells in which single cells had been verified by microscopy were then re-tested by the above method. Stability of antibody expression was judged on the number of wells showing antibody, the level of binding and the presence of any wells showing growth but little or no antibody. If any of the latter were found, a well showing high antibody secretion was then used to repeat stringent subcloning. This was repeated as necessary to obtain 100% of the subclones secreting equivalent quantities of antibody. Cells from selected wells were then expanded in culture, and used to prepare preliminary cell banks. The supernatant from those cultures was then subjected to specificity analysis.

EXAMPLE 9

Antibody Specificity

The antibody containing culture supernatants from the expansion cultures were subjected to specificity analysis by the following procedure. First, the titer appropriate for analysis was determined by dilution analysis. A dilution of antibody providing for approximately 50% of maximal binding was selected for proceeding to the next step. Second, binding to the atazanavir-BSA conjugate was examined at the above antibody dilution, in the presence of varying amounts of seven HIV protease inhibitor drugs. The data was subjected to analysis by non-linear regression curve fitting to a 4-parameter logistic function. That parameter which describes the concentration of the free drug which corresponds to 50% of the binding in the absence of free drug is termed the $ED_{50}$ for that drug. The specificity of the antibody can thus be described by comparing the $ED_{50}$ of the cognate drug, atazanavir, or atz $ED_{50}$ with the other values for other drugs fitted from those data according to the following equation (using nelfinavir data for this example):

$$\% \text{ cross-reactivity} = \frac{atz\ ED_{50}}{nel\ ED_{50}} \times 100.$$

The four parameter logistic function used is $$ODx = \frac{OD\ \max}{\left(1 + \left(\frac{ED_{50}}{X}\right)^S\right)} - OD\ \min$$

where S is the curvature parameter, ODmax is the optical density with 0 drug concentration, ODmin is the optical density of the background of the instrument, and ODx is the optical density observed at drug concentration X in moles/liter (M/L).

Table 2 shows the specificities of subclones of the cell lines shown in Table 1. Atazanavir metabolite is 4-pyridin-2-yl-benzoic acid (Synchem, Inc.). The antibodies tested were shown to be highly specific for atazanavir. Cross-reactivity testing at a 30-fold increase in relative concentration of the compounds tested showed no deflection, indicating competition inhibition.

TABLE 2

Specificity of selected stabilized subclones of atazanavir clones

| | ATZ 3.1 | | ATZ 4.1 | |
|---|---|---|---|---|
| | % Cross Rx | $ED_{50}$ (M/L) | % Cross Rx | $ED_{50}$ (M/L) |
| Atazanavir | 100 | $7 \times 10^{-7}$ | 100 | $4.4 \times 10^{-6}$ |
| Atazanavir metabolite | <1 | $>2 \times 10^{-6}$ | <1 | $>2 \times 10^{-6}$ |
| Saquinavir | <1 | $>2 \times 10^{-6}$ | <1 | $>2 \times 10^{-6}$ |
| Nelfinavir | <1 | $>2 \times 10^{-6}$ | <1 | $>2 \times 10^{-6}$ |
| Indinavir | <1 | $>2 \times 10^{-6}$ | <1 | $>2 \times 10^{-6}$ |
| Amprenavir | <1 | $>2 \times 10^{-6}$ | <1 | $>2 \times 10^{-6}$ |
| Ritonavir | <1 | $>2 \times 10^{-6}$ | <1 | $>2 \times 10^{-6}$ |
| Lopinavir | <1 | $>2 \times 10^{-6}$ | <1 | $>2 \times 10^{-6}$ |

EXAMPLE 10

Concentration-response Curve for Atazanavir

Figure 2:
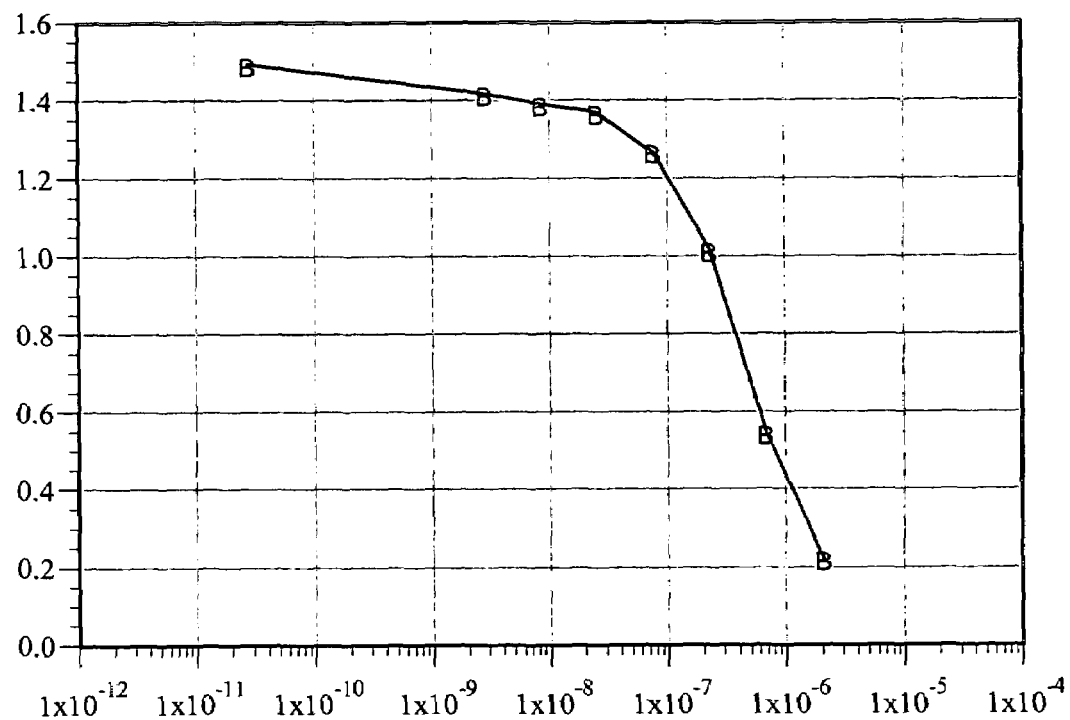
FIG. 2 is a concentration-response curve plotting the results from Example 10 using atazanavir-BSA conjugate 7 and antibody ATZ 4.1 of the present invention.

The ELISA assay used for specificity testing was used to produce a concentration-response curve using atazanavir-BSA conjugate 7, atazanavir free drug, and antibody ATZ 4.1. The concentration of atazanavir in moles/liter is plotted on the X-axis, and the response in absorbance at 4 minutes at a wavelength of 450 nm is plotted on the Y-axis. The resulting data is shown in FIG. 2 and indicates that the effective assay range is from $2\times10^{-8}$ to $2\times10^{-6}$ molar, or 0.16 µg/ml to 16 µg/ml.

Murine hybridoma ATZ 4.1 was deposited with the American Type Culture Collection (ATCC) on Oct. 19, 2004 and assigned ATCC No. PTA-6257.

What is claimed is:

1. A compound having the structure

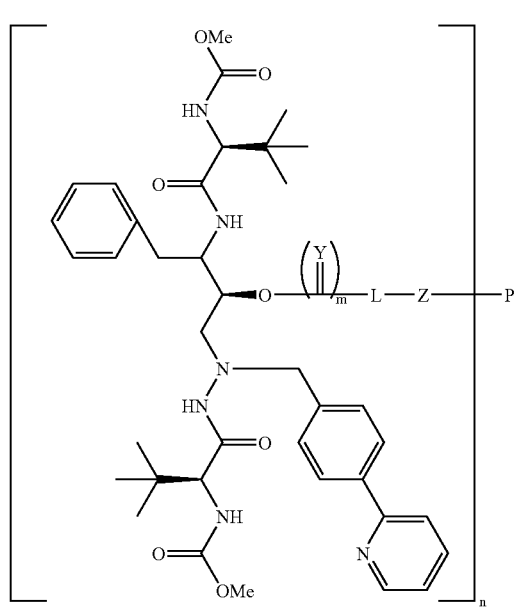

wherein Y is O, S, or NH, m is 0 or 1, L is a linker comprising from 0 to 40 carbon atoms arranged in a straight chain or a branched chain, saturated or unsaturated, and further comprising up to two ring structures and 0–20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

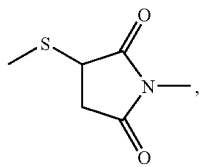

P is selected from the group consisting of polypeptides, polysaccharides and synthetic polymers, and n is a number from 1 to 50 per 50 kilodaltons molecular weight of P.

2. The compound of claim 1 wherein Y is O, m is 1, and P is selected from the group consisting of polypeptides and polysaccharides.

3. The compound $O^c$-[4'-(succinimido-oxycarbonyl)-benzoyl-aminocaproyl]-atazanavir conjugate with BSA.

4. The compound $O^c$-(succinimido-oxycarbonyl-butyryl-aminocaproyl)-atazanavir conjugate with KLH.

5. The compound $O^c$-(succinimido-oxycarbonyl-butyryl-aminocaproyl)-atazanavir.

6. The compound $O^c$-[4'-(succinimido-oxycarbonyl)-benzoyl-aminocaproyl]-atazanavir.

7. A compound having the structure

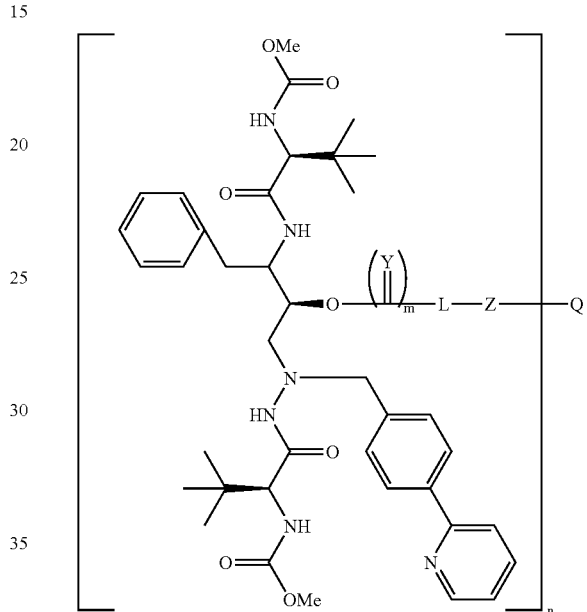

wherein Y is O, S, or NH, m is 0 or 1, L is a linker comprising from 0 to 40 carbon atoms arranged in a straight chain or a branched chain saturated or unsaturated, and further comprising up to two ring structures and 0–20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

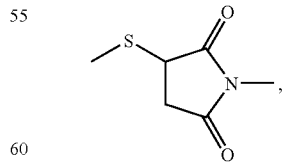

Q is selected from the group consisting of non-isotopic labels, and n is a number from 1 to 50 per 50 kilodaltons molecular Q.

8. The compound of claim 7 wherein Y is O, m is 1, and Q is selected from the group consisting of non-isotopic labels.

9. An antibody generated in response to a compound having the structure

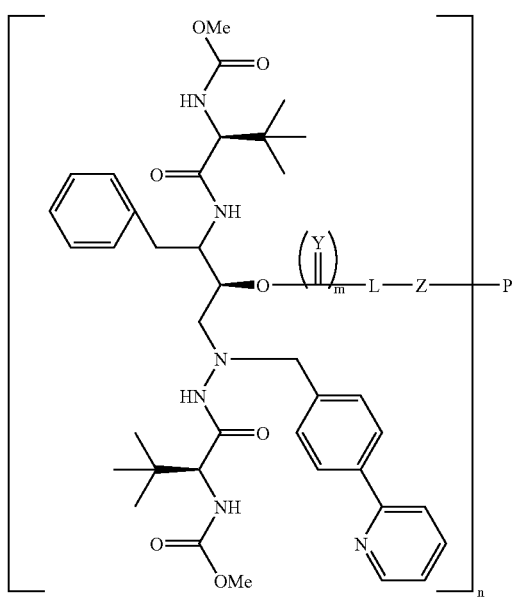

wherein Y is O, S, or NH, m is 0 or 1, L is a linker comprising from 0 to 40 carbon atoms arranged in a straight chain or a branch chain, saturated or unsaturated, and further comprising up to two ring structures and 0–20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, and

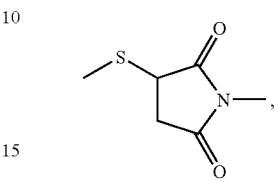

P is selected from the group consisting of polypeptides, a polysaccharides, and synthetic polymers, and n is a number from 1 to 50 per 50 kilodaltons molecular weight of P.

10. A monoclonal antibody specific for atazanavir having less than 1% cross-reactivity with an HIV protease inhibitor selected from the group consisting of saquinavir, nelfinavir, indinavir, amprenavir, ritonavir, and lopinavir.

11. A monoclonal antibody specific for atazanavir having less than 1% cross-reactivity with 4-pyridin-2-yl-benzoic acid.

12. Murine hybridoma ATZ 4.1 having ATCC No. PTA-6257.

* * * * *

UNITED STATES PATENT AND TRADEMARK OFFICE
CERTIFICATE OF CORRECTION

PATENT NO. : 7,157,561 B2  Page 1 of 1
APPLICATION NO. : 10/982611
DATED : January 2, 2007
INVENTOR(S) : Richard Hui et al.

It is certified that error appears in the above-identified patent and that said Letters Patent is hereby corrected as shown below:

On Title Page (54) change "METHODS OF INHIBITING TRANSMISSION OF A COSTIMULATORY SIGNAL OF LYMPHOCYTES" to --ATAZANAVIR CONJUGATES AND ANTIBODIES USEFUL IN IMMUNOASSAY--

Signed and Sealed this

Sixth Day of March, 2007

JON W. DUDAS
*Director of the United States Patent and Trademark Office*